(12) United States Patent
Russell

(10) Patent No.: US 11,123,081 B2
(45) Date of Patent: Sep. 21, 2021

(54) SURGICAL CLIP APPLICATOR AND MANUFACTURING METHOD THEREFOR

(71) Applicant: Okay Industries, Inc., New Britain, CT (US)

(72) Inventor: Shawn H. Russell, Bristol, CT (US)

(73) Assignee: Okay Industries, Inc., New Britain, CT (US)

( * ) Notice: Subject to any disclaimer, the term of this patent is extended or adjusted under 35 U.S.C. 154(b) by 275 days.

(21) Appl. No.: 16/268,896

(22) Filed: Feb. 6, 2019

(65) Prior Publication Data

US 2019/0254679 A1 Aug. 22, 2019

Related U.S. Application Data

(60) Provisional application No. 62/631,902, filed on Feb. 18, 2018.

(51) Int. Cl.

| | |
|---|---|
| *A61B 17/128* | (2006.01) |
| *A61B 17/122* | (2006.01) |
| *B22F 3/22* | (2006.01) |
| *B22F 7/08* | (2006.01) |
| *B23K 26/55* | (2014.01) |
| *A61B 17/00* | (2006.01) |
| *B22F 3/10* | (2006.01) |
| *B22F 5/00* | (2006.01) |
| *A61B 17/29* | (2006.01) |
| *A61B 17/068* | (2006.01) |

(52) U.S. Cl.
CPC ........ *A61B 17/1285* (2013.01); *A61B 17/122* (2013.01); *B22F 3/225* (2013.01); *B22F 7/08* (2013.01); *B23K 26/55* (2015.10); *A61B 17/0682* (2013.01); *A61B 17/29* (2013.01); *A61B 2017/00526* (2013.01); *B22F 3/1017* (2013.01); *B22F 5/00* (2013.01); *Y10T 29/49988* (2015.01)

(58) Field of Classification Search
CPC .............. A61B 17/1285; A61B 17/122; A61B 2017/00526; A61B 17/29; A61B 17/0682; B23K 26/55; B22F 7/08; B22F 3/225; B22F 3/1017; B22F 5/00; Y10T 29/49988
See application file for complete search history.

(56) References Cited

U.S. PATENT DOCUMENTS

| | | | |
|---|---|---|---|
| 9,931,123 B2 * | 4/2018 | Blake, III | .......... A61B 17/1285 |
| 2006/0161182 A1 * | 7/2006 | Vandenbroek | ....... A61B 17/128 606/142 |

* cited by examiner

*Primary Examiner* — John C Hong
(74) *Attorney, Agent, or Firm* — Alix, Yale & Ristas, LLP

(57) ABSTRACT

A method for manufacturing a surgical clip applicator comprises metal injection molding a pair of jaws. The method further comprises stamping a U-shaped body portion having a pair of laterally spaced arms and an integral bridge extending between the arms to define a gap. The method comprises welding a jaw to a corresponding arm by electron beam welding or other welding processes and removing the bridge to form the clip applicator. In some embodiments, the bridge is optional.

13 Claims, 7 Drawing Sheets

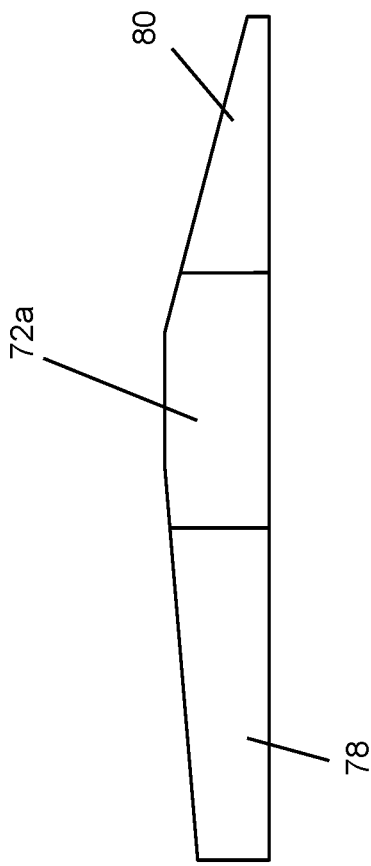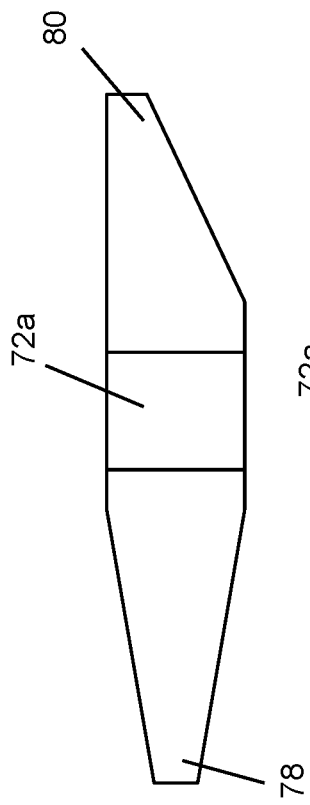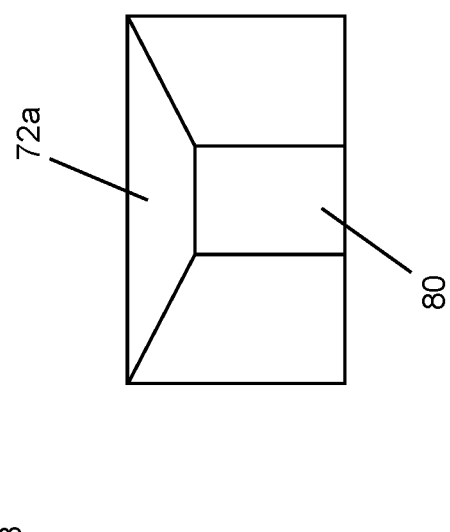
Figure 7A
Figure 7B
Figure 7C

SURGICAL CLIP APPLICATOR AND MANUFACTURING METHOD THEREFOR

BACKGROUND

The present disclosure relates generally to mechanical devices used in surgical procedures. More particularly, the present disclosure relates to a surgical clip applicator and methods of manufacturing a surgical clip applicator.

Surgical clips are used for occluding, ligating, and/or dividing body tissues and vessels during an open or minimally invasive surgical procedure. The clips are generally formed of metal wire, such as titanium alloy, and have an open-ended, "U-shaped" rectangular cross-section. Application of the clip to body tissue is typically effected by a compressive force and/or crimping action produced by a clip applicator. The compressive force and/or crimping action permanently deforms the clips, which makes them difficult to remove and/or reposition about the body tissue.

A disadvantage of many prior known clip applicators is that the manufacturing processes used to produce them are complex and expensive. Additionally, manufacturing processes that are simple and inexpensive typically lack design flexibility.

It is desirable to provide an improved clip applicator and method of manufacturing a clip applicator in a manner that fulfills one or more of the disadvantages described above.

SUMMARY

According to aspects illustrated herein, a clip applicator (hereafter, "applicator") is configured to receive a surgical clip and apply the surgical clip to body tissue of a patient during a surgical procedure. The applicator includes of a shaft which extends from a base end to a tapered transition end. The transition end of the shaft defines a pair of laterally-opposed radial cutouts. A body portion of the applicator extends from the shaft and has a pair of laterally-spaced arms which extend from a U-shaped neck. The arms of the body portion define a first gap of the applicator. In use, the arms flex inwardly into the first gap to apply a compressive force on the surgical clip.

In a pre-form state, a bridge may span the first gap and connect to each arm to stabilize the arms during the manufacturing process. The bridge is optional in some embodiments. A pair of laterally-spaced jaws extends from the body portion and defines a second gap. The width between each arm is less than the width between each jaw, such that the width of the second gap is greater than the width of the first gap. The bridge is preferably removed to substantially complete the manufacturing of the applicator. When the bridge is removed, the first and second gaps are merged into one gap defined between each corresponding arm and each corresponding jaw. In use, the arms and jaws flex inwardly into the merged gap to facilitate application of the compressive force on the surgical clip.

According to aspects illustrated herein, a method of manufacturing the clip applicator comprises a first step that includes metal injection molding a pair of jaws. A second step includes stamping a U-shaped body portion having a pair of laterally-spaced arms and an integral bridge spanning a gap defined between the arms. A third step includes welding each of the jaws to the corresponding arm using any number of welding processes, including but not exclusively, electron beam welding, laser welding, and resistance welding. The bridge, which is optional, stabilizes the arms of the body portion during the electron beam welding process. A fourth step includes trimming and/or removing the bridge from the applicator workpiece. A fifth step may include using a finishing process of various forms.

BRIEF DESCRIPTION OF THE DRAWINGS

Aspects of an embodiment of a surgical clip applicator and manufacturing process therefor will be described in reference to the drawings, wherein like numerals reflect like elements:

FIG. 7A is an enlarged top view of a jaw member of the applicator of FIG. 1;

FIG. 7B is a side view of the jaw member of FIG. 6A;

FIG. 7C is a front view of the jaw member of FIG. 6A; and

DETAILED DESCRIPTION

Figure 1:
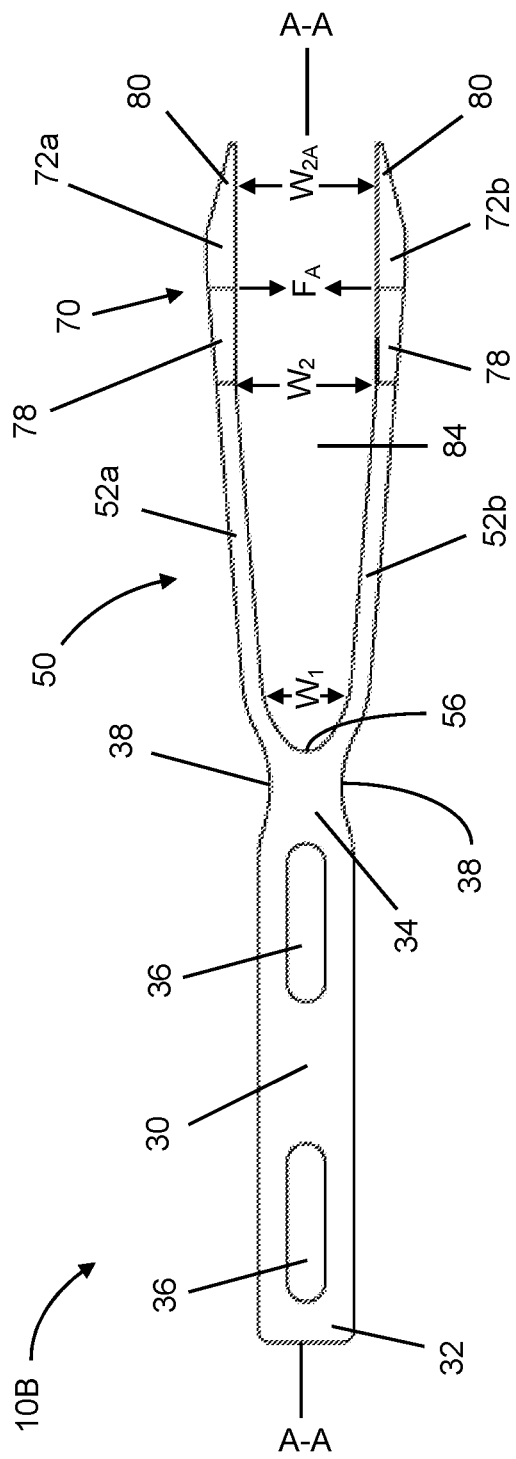
FIG. 1 is a diagrammatic top view of a surgical clip applicator (hereafter, "applicator") according to aspects of the disclosure.
Figure 2:
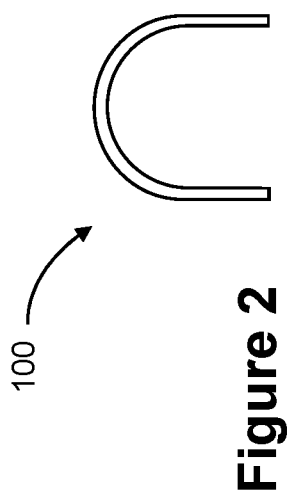
FIG. 2 is a top view of a surgical clip for the applicator of FIG. 1.

An embodiment of a surgical clip applicator (hereafter, "applicator") and a manufacturing method therefor according to aspects of the disclosure will now be described with reference to FIGS. 1-8. The finished applicator will generally be referred to by the reference numeral 10. Various materials, methods of construction, methods of manufacture, and methods of fastening will be discussed in the context of the disclosed embodiments. Those skilled in the art will recognize known substitutes for the materials, manufacturing methods, and fastening methods, all of which are contemplated as compatible with the disclosed embodiments and are intended to be encompassed by the appended claims.

Figure 3:
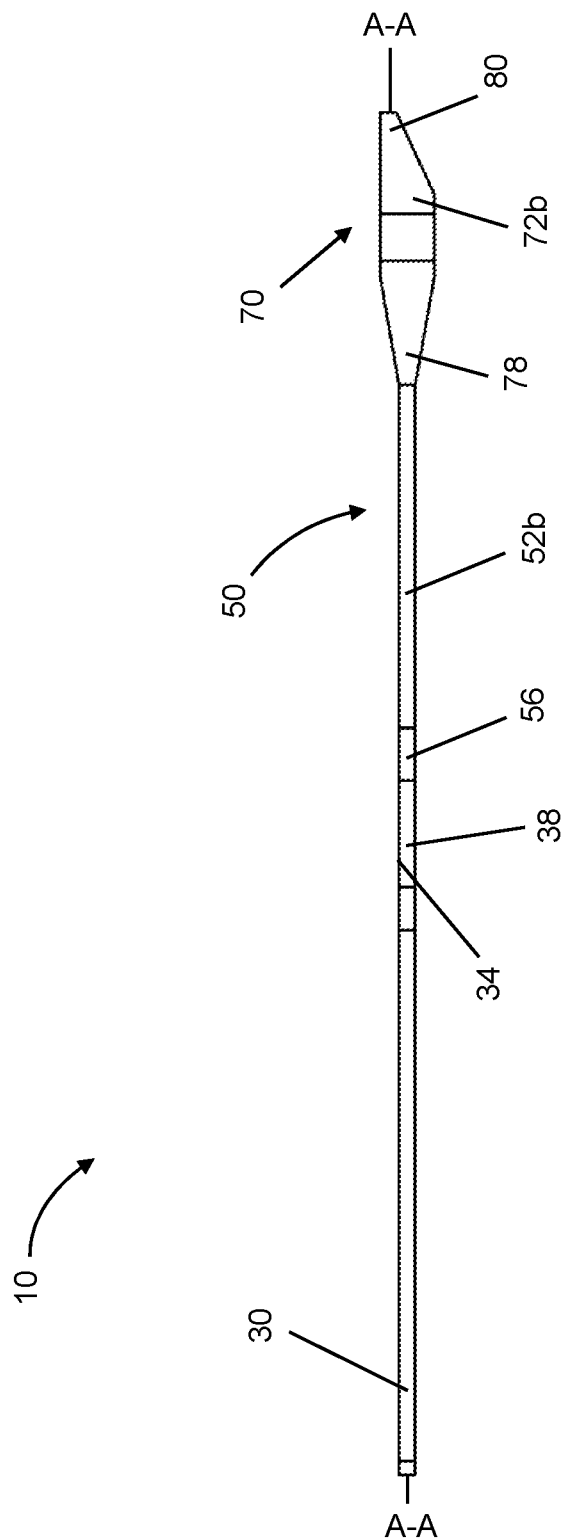
FIG. 3 is a side view of the applicator of FIG. 1.

As shown in FIGS. 1 and 3, the applicator 10 in a preferred finished form, is comprised of an elongated shaft 30, a body portion 50 having a pair of laterally-spaced arms 52a, 52b and defining a first gap 54, and a pair of laterally-spaced jaws 72a, 72b defining a second gap 74. During manufacturing, intermediate workpieces may employ a bridge 76 (not shown in FIGS. 1 and 3 as further described below) spanning and dividing the first and second gaps 54, 74 to stabilize each arm 52a, 52b during manufacturing. The bridge is optional for some embodiments.

The applicator 10 is configured to receive a surgical clip 100 which is to be applied to body tissue of a patient during a surgical procedure. As shown in FIG. 1, the applicator 10 is capable of clinching and/or flexing the jaws 72a, 72b inwardly to apply a compressive force $F_A$ to crimp and/or close the clip 100 on the body tissue to occlude, ligate, and/or divide the body tissue.

The applicator 10 may be constructed of metal (such as titanium, tantalum, inconel, brass, cobalt, chrome, low and high-strength low alloy steels with a thicknesses of up to 0.5 inches, stainless steel, aluminum, nitinol, kovar, monel, medical-grade plastics, and the like), but a person having ordinary skill in the art would recognize that other materials may be compatible with the disclosed embodiment.

As shown in FIG. 1, the applicator 10 has a central longitudinal axis A-A which provides a convenience reference. The shaft 30 extends from a base end 32 to a tapered transition end 34. The shaft 30 may include any number of openings/apertures of various shapes 36. The transition end 34 connects the shaft 30 to the body portion 50 and includes a pair of laterally-opposed radial cutouts 38. In a preferred embodiment, the base end 32 may have a width of at least 0.15 inches and no more than 0.45 inches. The transition end 34 may have a width that is less than the width of the base end 32.

Figure 4:
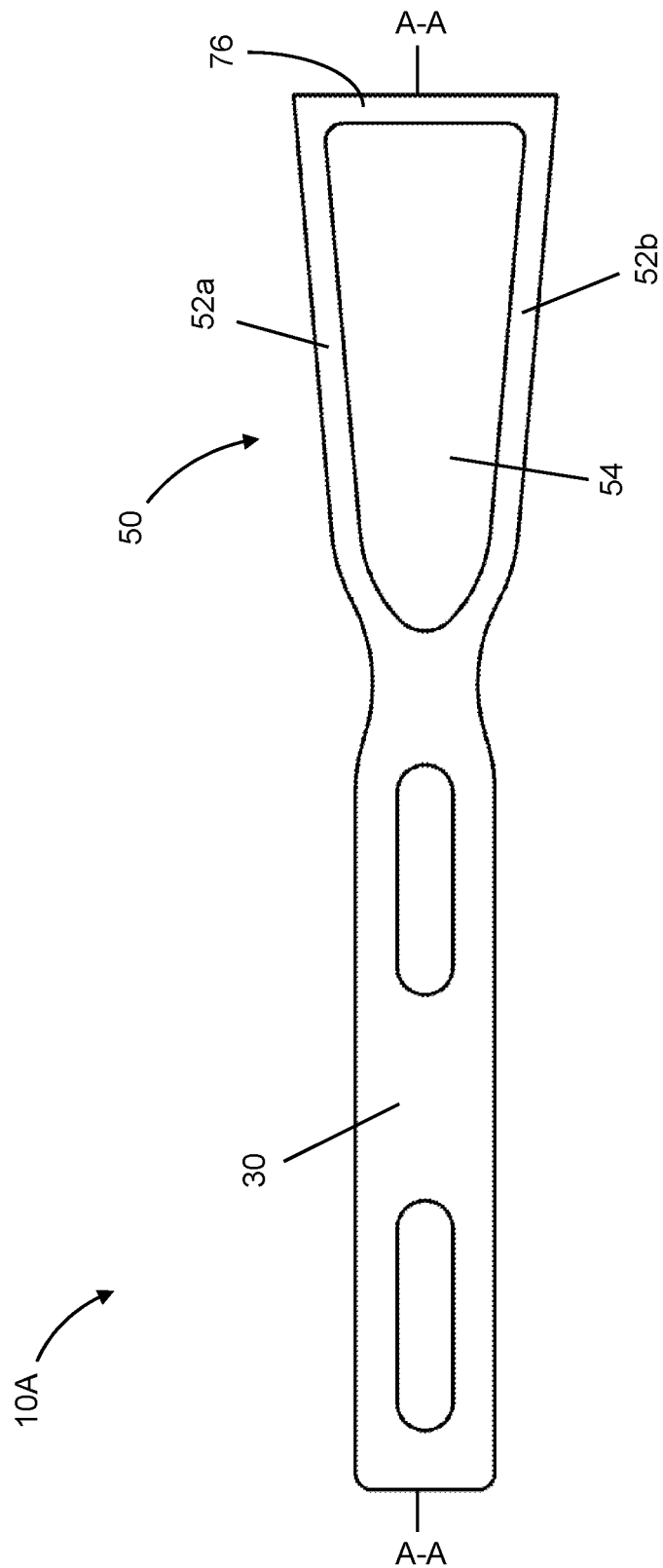
FIG. 4 is an enlarged partial top view of a workpiece at a manufacturing stage for the applicator of FIG. 1.
Figure 5:
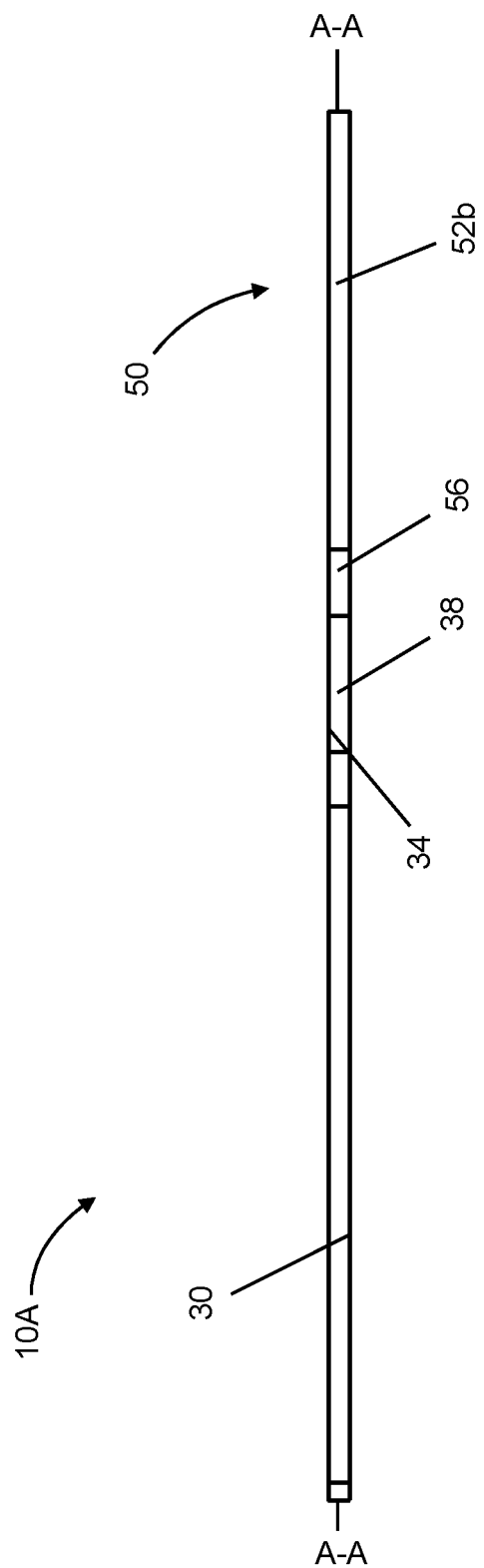
FIG. 5 is a side view of the workpiece of FIG. 4.

As best shown in FIG. 4, the body portion 50, including the bridge 76, is stamped or pressed to form workpiece 10A. The stamping process usually involves placing flat, cold sheet metal, in either blank or coil form, into a stamping press where a tool and die surface forms the metal into a new shape. Stamping includes a variety of sheet-metal forming manufacturing processes, such as punching using a machine press or stamping press, blanking, embossing, bending, flanging, and coining. Stamping may be a single-stage operation, where every stroke of the press produces a desired form on the sheet metal part, or the stamping may occur through a series of stages. The stamping process is usually carried out on sheet metal, but can also be used on other materials.

Figure 6:
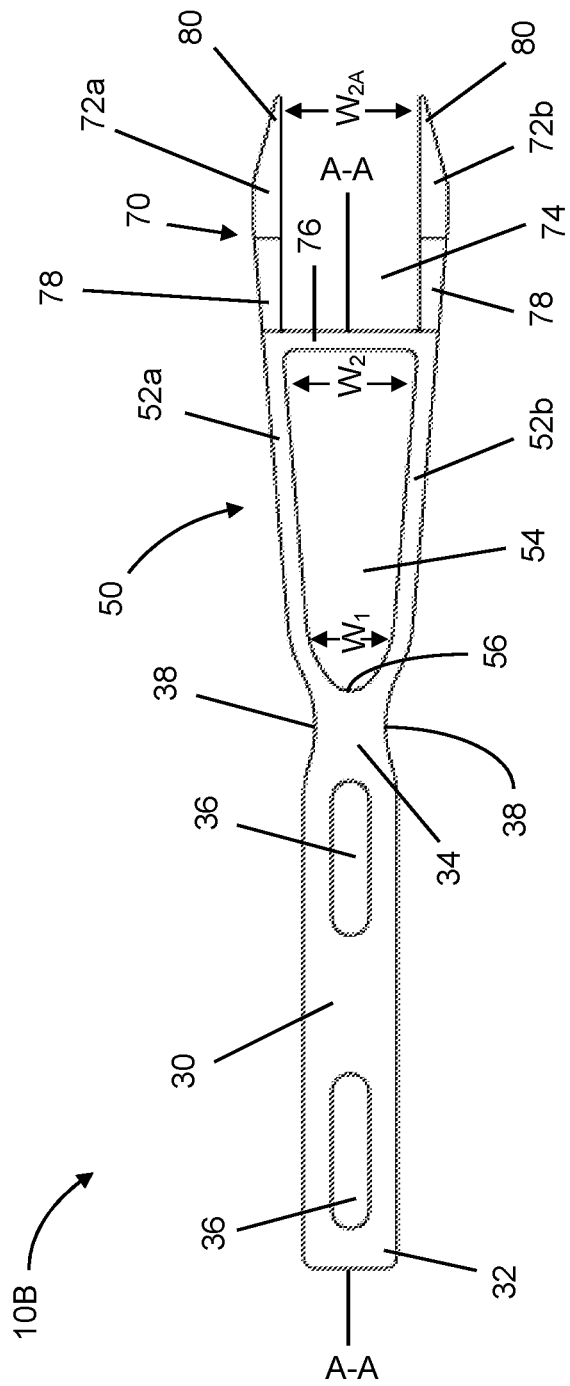
FIG. 6 is a diagrammatic top plan view of a second workpiece at a subsequent manufacturing stage for the applicator of FIG. 1.

As best illustrated by FIGS. 1, 4 and 6, the body portion 50 in a manufacturing includes a pair of laterally-spaced arms 52a, 52b extending from a U-shaped neck 56. A first gap 54 is defined between each arm 52a, 52b. The arms 52a, 52b extend out to an integral bridge 76. The bridge, which may be optional, spans the first gap 54 to connect to and stabilize each arm 52a, 52b during a welding or connecting process which may be electron beam welding, laser welding or resistance welding. As the arms 52a, 52b extend out from the neck 56, the arms 52a, 52b diverge outwardly and expand the first gap 54 defined therebetween from a first width $W_1$ to a second width $W_2$. Each arm 52a, 52b may have a width of at least 0.025 inches and no more than 0.075 inches. The first gap 54 defined between the arms 52a, 52b may have a width of at least 0.025 inches and no more than 0.50 inches.

As shown in FIGS. 1, 3, 4, 6 and 7A-7C of the disclosed embodiment, jaws 72a, 72b are metal injection molded (MIM) members which are preferably substantially identical in shape. The MIM process usually involves but is not limited to combining metal powders with polymers such as wax and polypropylene binders to produce a "feedstock" mix that is injected as a liquid into a jaw-shaped mold using plastic injection molding machines. The mold is cooled and ejected from the mold. Next, a portion of the binder material is removed using a solvent, a thermal furnace, a catalytic process, and/or a combination of methods. The resulting part is fragile and porous. To improve handling, often debinding and sintering processes are combined into a single process. Sintering heats the powder to temperatures near the melting point in a protective atmosphere furnace to densify the particles using capillary forces. MIM parts are often sintered at temperatures nearly high enough to induce partial melting in a process termed liquid phase sintering. For example, a stainless steel might be heated to 1350 to 1400 degrees Celsius. High diffusion rates lead to high shrinkage and densification.

As shown in FIG. 6 of the enclosed embodiment, after the jaw 70 is formed through the MIM process and the body portion 50 is produced through either the stamping, wire EDM (electrical discharge machining), chemical etching, or laser cutting process, the jaw 70 is welded via electron beam, laser or resistance welding to the body 50. The EBW (electron beam welding) process is a fusion welding process which usually involves applying a beam of high-velocity electrons to heat a weld joint of two materials to be joined—the jaw 70 and the body portion 50. The parts melt and flow together as the kinetic energy of the electrons is transformed into heat upon impact. EBW is often performed under vacuum conditions to prevent dissipation of the electron beam. As shown in FIG. 1, once the jaw 70 and body portion 50 undergo the EBW or other welding process, if employed, the bridge 76 of an applicator workpiece 10A is trimmed and/or removed so that the first and second gaps 54, 74 become one merged gap 84. In use, the arms 52a, 52b and jaws 70a, 70b flex inwardly into the merged gap 84 to apply the compressive force $F_A$ on the surgical clip.

As shown in FIG. 6 for a subsequent stage workpiece 10B, a pair of laterally-spaced jaws 72a, 72b extends longitudinally from the body portion 50. A second gap 74 is defined between the jaws 72a, 72b. Each jaw 72a, 72b extends from a base 78 that is connected to a corresponding arm 52a, 52b. Each jaw 72a, 72b widens from the base 78 to a center and tapers from the center to a tip 80. As the jaws 72a, 72b extend, the second gap 74 widens from a width equal to or greater than the second width $W_2$ of the first gap 54 to a second width $W_{2A}$ of the second gap 74. The difference in first width $W_1$ of the first gap 54 and the second width $W_{2A}$ of the second gap 74 allows for an inward flexure between the arms 52a, 52b and jaws 72a, 72b. The second width $W_{2A}$ of the second gap 74 has a width of at least 0.25 inches and no more than 0.75 inches.

Figure 8:
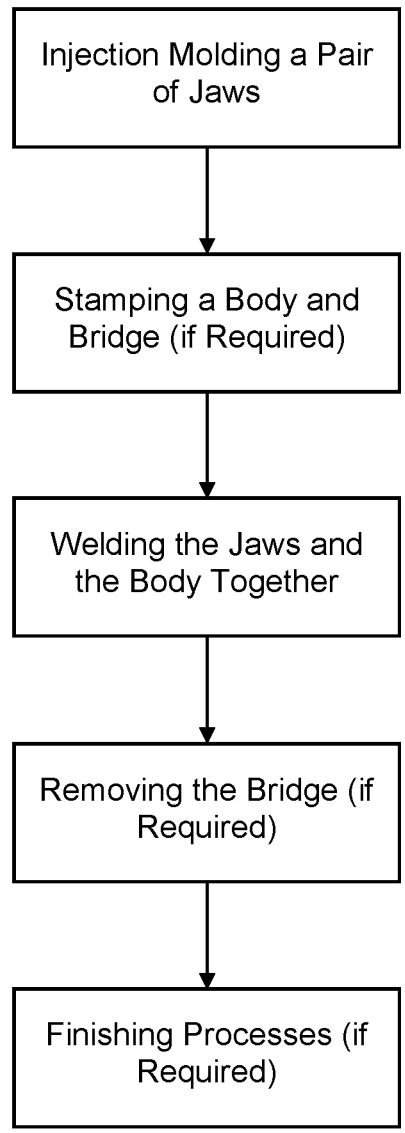
FIG. 8 is a block diagram describing the steps and a step sequence of a method of manufacturing the applicator of FIG. 1.

As described in FIG. 8, once the applicator 10 is formed, other finishing processes such as electropolishing, tumbling, coating, plating, passivation, and or light machining may be performed as required.

While embodiments of the disclosed clip applicator 10 and the manufacturing method therefor having been set forth for purposes of illustration, the foregoing description should not be deemed a limitation of the invention. Accordingly, various modifications, adaptations and alternatives may occur to one skilled in the art without departing from the spirit of the invention and the scope of the claimed coverage.

The invention claimed is:

1. A method of manufacturing a clip applicator comprising:
    metal injection molding a pair of jaws;
    stamping, wire EDM, chemical etching, or laser cutting a generally U-shaped body portion having a pair of laterally-spaced arms and an integral bridge member extending between said arms to define a first gap;
    welding each of said jaws to a corresponding arm to define second gap; and
    removing the integral bridge member.

2. The method of claim 1 further comprising configuring and positioning the jaws so that they are mirror images of each other.

3. The method of claim 1 wherein the step of welding each of said jaws further comprises electron beam welding, laser welding or resistance welding.

4. The method of claim 1 further comprising forming a merged gap from said first and second gaps upon removing the bridge member.

5. The method of claim 1 wherein the step of stamping a generally U-shaped body portion further comprises forming the arms to extend from a U-shaped neck and further comprising forming a shaft which projects from said neck.

6. The method of claim 1 further comprising applying at least one finishing process to the clip applicator.

7. A method of manufacturing a clip applicator comprising:
   metal injection molding a pair of jaws;
   stamping a workpiece comprising a shaft and a body portion having a pair of laterally-spaced arms defining a gap defined between the arms;
   positioning each of said jaws adjacent an end of an arm; and
   welding each of said jaws to a corresponding arm.

8. The method of claim 7 wherein the step of stamping the workpiece comprises forming a body portion so the arms extend from a U-shaped neck.

9. The method of claim 7 wherein the step of welding each of said jaws further comprises electron beam welding.

10. The method of claim 7 further comprising forming a bridge extending between the pair of laterally spaced arms and removing the bridge after welding each of said jaws to a corresponding arm to form a second workpiece.

11. The method of claim 10 further comprising finishing the second workpiece by a process selected from the group consisting electropolishing, plating, tumbling, coating and machining.

12. The method of claim 7 wherein the step of welding further comprising laser welding.

13. The method of claim 7 wherein the step of welding further comprising resistance welding.

\* \* \* \* \*